United States Patent
Rietzel

(10) Patent No.: US 8,772,742 B2
(45) Date of Patent: Jul. 8, 2014

(54) RADIATION THERAPY SYSTEM AND METHOD FOR ADAPTING AN IRRADIATION FIELD

(75) Inventor: Eike Rietzel, Darmstadt (DE)

(73) Assignee: Siemens Aktiengesellschaft, München (DE)

(*) Notice: Subject to any disclaimer, the term of this patent is extended or adjusted under 35 U.S.C. 154(b) by 1797 days.

(21) Appl. No.: 11/899,805

(22) Filed: Sep. 7, 2007

(65) Prior Publication Data

US 2008/0071131 A1 Mar. 20, 2008

Related U.S. Application Data

(60) Provisional application No. 60/845,030, filed on Sep. 15, 2006.

(30) Foreign Application Priority Data

Sep. 15, 2006 (DE) .......................... 10 2006 044 139

(51) Int. Cl.
*A61N 5/10* (2006.01)

(52) U.S. Cl.
CPC .................................... *A61N 5/1071* (2013.01)
USPC .............................. 250/492.3; 378/65; 378/64

(58) Field of Classification Search
USPC ..................................... 250/492.3; 378/65, 64
See application file for complete search history.

(56) References Cited

U.S. PATENT DOCUMENTS

| | | |
|---|---|---|
| 6,687,330 B2 | 2/2004 | Hernandez-Guerra |
| 6,717,162 B1 | 4/2004 | Jongen |
| 6,796,943 B2 | 9/2004 | Mochizuki |
| 6,993,112 B2 * | 1/2006 | Hesse .............................. 378/65 |
| 2005/0096515 A1 | 5/2005 | Geng |
| 2005/0201516 A1 | 9/2005 | Ruchala et al. |
| 2006/0074292 A1 | 4/2006 | Thomson et al. |

FOREIGN PATENT DOCUMENTS

| | | |
|---|---|---|
| EP | 0 986 070 A1 | 3/2000 |
| JP | 2001259059 A | 9/2001 |
| JP | 2001259060 A | 9/2001 |
| JP | 2001327514 A | 11/2001 |
| JP | 2002165894 A | 6/2002 |

(Continued)

OTHER PUBLICATIONS

Japanese Office Action dated Jun. 1, 2012 for corresponding Japanese Patent Application No. 2007-237915 with English translation.

(Continued)

*Primary Examiner* — Kiet T Nguyen
(74) *Attorney, Agent, or Firm* — Lempia Summerfield Katz LLC

(57) ABSTRACT

A radiation therapy system for irradiating a target volume with a particle beam is provided. The radiation therapy system includes a radiation source that is operable to output an adjustable irradiation field that includes a particle beam that is scanned point by point over the target volume. A 3D imaging device may obtain a 3D radiation treatment data set in a radiation treatment phase. An adaptation unit adapts the irradiation field to a change in position and/or shape of the target volume in the radiation treatment phase. The adaptation unit compares the 3D radiation treatment data set with a 3D planning image data set furnished and obtains a transformation that describes the change in position and/or shape of the target volume. The adaptation unit transforms an irradiation field based on the transformation.

8 Claims, 2 Drawing Sheets

(56) References Cited

FOREIGN PATENT DOCUMENTS

| | | |
|---|---|---|
| JP | 2002534138 A | 10/2002 |
| JP | 2004000499 A | 1/2004 |
| JP | 2005185336 A | 7/2005 |
| WO | WO 2006/018761 A1 | 2/2006 |

OTHER PUBLICATIONS

Japanese Office Action dated Jan. 8, 2013 for corresponding Japanese Patent Application No. 2007-237915 with English translation.

German Office Action dated May 7, 2007 with English translation.

Rietzel E., et al., "Four-Dimensional Image-Based Treatment Planning: Target Volume Segmentation and Dose Calculation in the Presence of Respiratory Motion", Int. J. Radiat. Oncol. Biol. Phys., vol. 61, No. 5 (2005), pp. 1535-1550.

Pedroni, Eros, The 200-MeV proton therapy project at the Paul Scherrer Institute: conceptual design and practical realization, 2389 Medical Physics, 22 (1995), January, No. 1, Woodbury, NY, accepted for publication Aug. 24, 1994, pp. 37-53.

Christoph Bert, "Bestrahlungsplanung für bewegte Zielvolumina in der Tumortherapie mit gescanntem Kohlenstoffstrahl," Dissertation: TU Darmstadt, Fachbereich Physik, Feb. 3, 2006.

Radhe Mohan, et al., "Use of Deformed Intensity Distributions for On-line Modification of Image-Guided IMRT to Account for Interfractional Anatomic Changes," Int. J. Radiation Oncology Biol. Phys., vol. 61, No. 4, pp. 1258-1266, 2005.

Laurence E. Court, et al., "An Automatic CT-Guided Adaptive Radiation Therapy Technique by Online Modification of Multileaf Collimator Leaf Positions for Prostate Cancer," Int. J. Radiation Oncology Biol. Phys., vol. 62, No. 1, pp. 154-163, 2005.

Laurence E. Court, et al., "Automatic Online Adaptive Radiation Therapy Techniques for Targets with Significant Shape Change: A Feasibility Study," Phys. Med. Biol., vol. 51, No. 27, pp. 2493-2501, 2006.

Luis Ibañez, et al., "The ITK Software Guide, Second Edition, Updated for ITK version 2.4," Nov. 21, 2005.

Notice of Opposition to European Patent EP1900392 dated Aug. 12, 2011.

* cited by examiner

RADIATION THERAPY SYSTEM AND METHOD FOR ADAPTING AN IRRADIATION FIELD

The present patent document claims the benefit of the filing date of German Patent Application No. DE 10 2006 044 139.7 and U.S. Provisional Patent Application Ser. No. 60/845,030, both filed Sep. 15, 2006, which are hereby incorporated by reference.

BACKGROUND

The present embodiments relate to a radiation therapy system for irradiating a target volume that may change position and/or shape over time.

Radiation therapy may use high-energy photons or particles. U.S. Pat. No. 6,687,330 B2 discloses radiation therapy that uses high-energy photons. A particle therapy system typically has an accelerator unit and a high-energy beam guidance system. A synchrotron or cyclotron may be used to accelerate the particles, such as protons or carbon or oxygen ions.

The high-energy beam transporting system transports the particles from the accelerator unit to one or more treatment rooms. A distinction is made between "fixed beam" treatment rooms and gantry-based treatment rooms. Particles arrive at the treatment site from a fixed direction in "fixed beam" treatment rooms. In a gantry-based treatment room, the particle beam may be aimed at the patient from various directions using a gantry.

A distinction may also be made between scanning and scattering. Scattering employs a large-area beam adapted to the dimensions of the volume to be irradiated Scanning scans a "pencil beam" with a diameter of a few millimeters to centimeters over the volume to be irradiated. When a scanning system is embodied as a grid scanning system, the particle beam is steered "point by point" to a volume element of a grid until such time as a previously defined number of particles has been applied. The volume elements in the scanning area are irradiated in succession; preferably, the expanse of the "pencil beams" that are side by side overlap. The particles for one volume element contribute to the dose within this volume element and along the entire path struck by the particles.

A monitoring and safety system of the particle therapy system may be used to direct a particle beam, characterized by the parameters wanted, into the appropriate treatment room. The parameters of a radiation treatment procedure, for example, in a treatment plan, are summarized as an irradiation field. The irradiation field includes an association of the particle with the volume element. The irradiation filed is defined by how many particles from which direction and with what energy, are supposed to strike the patient or the volume elements. The energy of the particles determines the penetration depth into the patient. For example, the energy of the particles may determine the site at which the maximum interaction with the tissue takes place in the particle therapy. The energy of the particles defines the site where the maximum dose is deposited. During the treatment, the maximum deposited dose is located inside the tumor (or in the case of other medical applications of the particle beam, in the particle target area).

The monitoring and safety system controls a positioning device, with which the patient is positioned relative to the particle beam. For carrying out the treatment plan, the patient should assume a position for the irradiation that matches the planning. Matching the position to the plan is done, for example, by 2D position verification. 2D position verification includes, for example, before the irradiation is performed, calibrating 2D images with images from the irradiation planning.

European Patent Disclosure EP 0 986 070 and "The 200-MeV Proton Therapy Project at the Paul Scherrer Institute: Conceptual Design and Practical Realization", E. Pedroni et al, Med. Phys. 22, 37-53 (1995) disclose particle therapy systems with a scanning system.

When planning a treatment, typically a plurality of irradiation fields, with different angles of incidence, are planned for individually. Each irradiation field is adapted to the scanning system. For example, each field is planned individually and its expanse is limited by a scanning range of the scanning system. The maximum deflection of the particle beam determines the scanning range. A distinction is made between 2D scanning (the particle beam deflection is in two directions) and 1D scanning. In 1D scanning, the patient is moved in increments, so that even a volume that is extensive in the second dimension can be irradiated.

Irradiation of a target volume in the radiation treatment phase may have a different position and/or size than was determined in the planning phase for setting up the irradiation field. This may be problematic because as a result of the change in location and/or size of the target volume, the target volume may not be located at the planned site in the patient despite position verification of the patient.

A similar situation arises in irradiation of targets that, for example, move because of respiration. These problems are discussed, for example, in E. Rietzel et al, "Four-Dimensional Image Based Treatment Planning: target volume segmentation and dose calculation in the presence of respiratory motion", Int. J. Radiation Oncology Biol. Phys. Vol. 61, No. 5, pp. 1535-1550, 2005. This article also discloses methods for segmentation that may be used for demarcating a tumor tissue. In radiooncology, segmentation and registering of image data are known.

SUMMARY

The present embodiments may obviate one or more of the drawbacks or limitations of the related art. For example, in one embodiment, the performance of an irradiation of a volume whose position and/or size varies is simplified. The embodiments will be discussed below predominantly in conjunction with a particle therapy system, but the same problems and solutions arise in photon therapy as well.

In one embodiment, an irradiation field is adapted for a target volume, which can change its position and/or shape in the patient over time. A 3D planning image data set, which may already be generated in a planning phase of the radiation therapy, is furnished together with an irradiation field planned on the basis of the 3D planning image data set. The irradiation field corresponds to an association of doses to be applied to individual volume elements of the target volume. In the radiation treatment phase, the patient is then prepared for the irradiation and positioned accordingly. Because of the later time of the irradiation session in comparison to the irradiation planning, the target volume may have changed its position and/or shape in the patient.

In one embodiment, the irradiation is adjusted to compensate for changes of the position and/or shape of the target volume in the patient. A 3D radiation treatment set is obtained in the radiation treatment phase. This 3D radiation treatment data set is registered with the 3D planning image data set. An associated transformation is obtained which in a matching coordinate system describes, for example, the displacement, scaling, shearing, and/or also deformation of the target volume. To take the change in the target volume into account, the irradiation field from the planning phase is adapted with this transformation to the radiation treatment phase. The 3D radiation treatment data set then three-dimensionally reproduces the target volume to be irradiated at the time of a radiation session, or, for example, during the radiation treatment phase.

The planned irradiation field, verified for the irradiation and checked, does not require reverification despite the change in the target volume. Slight changes in position and/or shape in the target volume may be taken into account quickly and easily in the radiation treatment phase. The doses of the irradiation field may be verified or adapted on the basis of the density distribution in the 3D radiation treatment data set in the respective inlet conduit, for example, for greater changes in position and/or shape in the target volume. The requisite precision in particle therapy in terms of the penetration depths of the particles may be assured.

In one embodiment, the irradiation field may be regularized. The irradiation field may be regularized for irradiation with a scanner. In another example, the irradiation field may be regularized whenever individual volume elements in the target volume change their spacing because of compression and no longer can be projected onto the grid of the scanner, for example. The doses may be interpolated via the radiation treatment grid. Even in the event of major changes in position and/or shape in the target volume, the irradiation plan may be used.

The registering may be done manually, in partly automated fashion, or in automated fashion. An operator, for example, marks matching points in the various 3D image data sets and on the basis of these input parameters has the transformation of the marked points calculated. A register may be made in automated fashion with the aid of Hounsfield values, which are significant for the target volume.

In one embodiment, motions of tissue that surrounds the target volume may be registered. These motions may be used for adaptation of the direction of incidence. These motions may, for example, have an influence on the direction of incidence, if this tissue must not be irradiated. Tissue regions located in the vicinity of the target volume, for example, which are to be spared, are kept out of the inlet conduit.

In one embodiment, a warning signal may be generated (for instance acoustically or visually) when the registering that the change in position and/or shape of the target volume exceeds a limit value. An operator may discontinue the radiation treatment phase, for example, if the operator assesses the changes as problematic. Alternatively, the operator may disable the warning signal and continue the irradiation with the adapted irradiation field.

In one embodiment, a radiation therapy system may include a radiation source for generating an irradiation field which is adjustable. The radiation therapy system may also include a 3D imaging device for obtaining a 3D radiation treatment data set in a radiation treatment phase of the radiation therapy. The radiation therapy system may include an adaptation unit, which may adapt the irradiation field to a change in position and/or shape present in the radiation treatment phase. The adaptation unit is embodied to register the 3D irradiation data with a furnished 3D planning image data set and to obtain an associated transformation which describes the change in position and/or shape of the target volume. The adaptation unit is embodied for transforming a furnished planning field with the obtained transformation and adapting it to the change in position and/or shape of the target volume in the radiation treatment phase. The planning field is planned in a planning phase by association of doses to be applied with volume elements of the target volume based on the 3D planning image data set.

The radiation therapy system is able, without reverification of an irradiation field, to use this irradiation field with altered target volumes. This speeds up the radiation therapy, since recalculations of irradiation fields that would otherwise be needed are dispensed with.

In one embodiment, the radiation source may output a high-energy particle beam or photon beam. This beam is adjustable in terms of its energy, beam direction, shape, grid scale, energy distribution, and/or intensity. The changes in the applied radiation may be made on the basis of the transformation. Changes may be necessary, for example, whenever the adaptation unit is embodied for verifying or adapting doses of the irradiation field on the basis of the density distribution in the 3D radiation treatment data set in the particular inlet conduit. Adjustment changes may be needed whenever the adaptation unit is embodied for regularizing the irradiation field on the basis of the change in position and/or shape, and interpolating it to a predetermined radiation treatment grid. Changes in the applied radiation may also be required whenever the adaptation unit is embodied for adapting the direction of incidence, for example, to a change in position and/or shape of a volume surrounding the target volume. Overdoses in tissue, which are to be spared, may, for example, be prevented.

DETAILED DESCRIPTION

Figure 1:
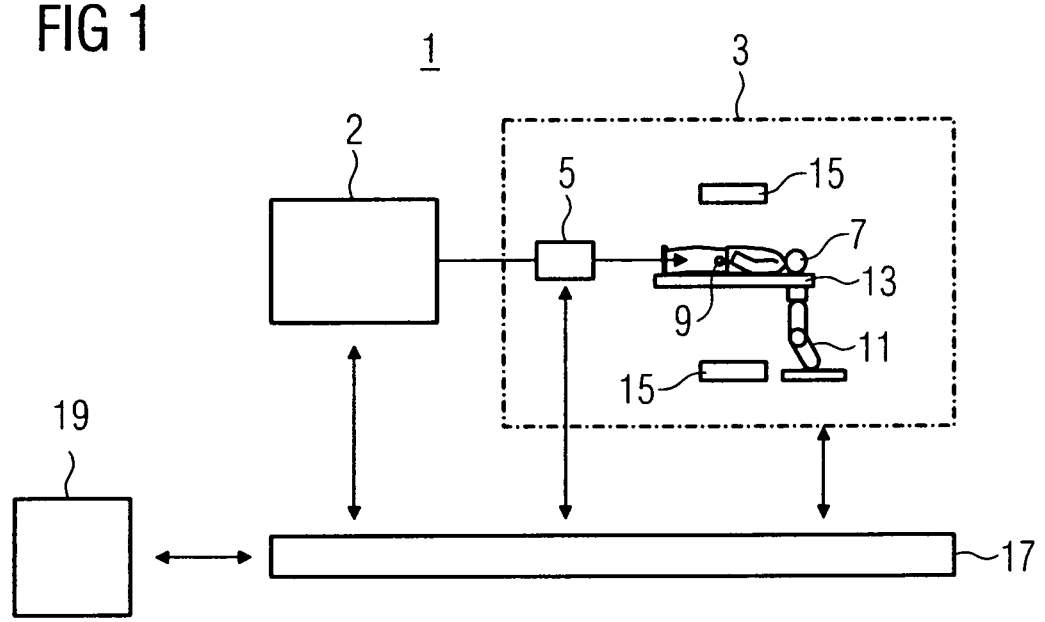
FIG. 1 illustrates one embodiment of a particle therapy system.

In one embodiment, as shown in FIG. 1, a radiation therapy system 1 includes a radiation source 2 and an irradiation site 3. The radiation therapy system 1 may include a scanning system 5 and a patient 7 aligned with it. In the case of a particle therapy system, the radiation source 2, for example, has an accelerator system (e.g., synchrotron and cyclotron) and a high-energy beam supply. There, particles and ions, such as protons or carbon ions, are accelerated to energies of up to several 100 MeV. With the scanning system 5, the beam may be adjusted in its beam position, such as parallel within a scanning region.

In FIG. 1, as an example, a prostate of the patient 7 is to be irradiated. The location of the prostate varies daily, depending on how full the bladder and intestines are. The prostate is one example of a target volume 9 that as a function of time changes in terms of its position and/or size over time. The reasons for such changes may also be shrinkage or growth of the tumors and changes in the weight and shape based on how full nearby organs are. On a shorter-term time scale, motions, which cause a change in position and/or size, may be caused by peristalsis, the heartbeat, or respiration. With suitably high-speed computing power, even such brief changes in position may be taken into account in the irradiation.

In one embodiment, as shown in FIG. 1, the radiation therapy system 1 includes a positioning device 11 (for instance robot-based). The positioning device 11 may flexibly adjust the alignment of the patient support 13. Variations in the irradiation position or angle of incidence may be done in terms of the patient by using the patient positioning device 11 and/or in terms of the beam delivery using the scanner 5 and/or by rotating a gantry.

In one embodiment, as shown in FIG. 1, the radiation therapy system 1 includes a schematic 3D imaging device 15. The schematic 3D imaging device 15 performs 3D imaging of the target volume and its surroundings in the radiation treatment phase, for example, shortly before the application of the radiation is tripped.

In one embodiment, as shown in FIG. 1, the radiation therapy system 1 includes an adaptation device 17. The adaptation device 17 may be, for example, a monitoring system. The adaptation device 17 may cause adjustments to be made in the patient positioning device 11 and the scanner 5, a gantry angle, and radiation parameters of the radiation source 2 (such as energy, energy distribution, intensity, and so forth). The adaptation device 17 may be in direct contact with a workstation 19 for treatment planning that, for example, has a planning CT unit and suitable planning programs for calculating a dosage distribution of an irradiation field. The adaptation device 17 may, for example, directly, obtain a 3D planning image data set with an associated irradiation field or irradiation fields from the planning workstation 19. The adaptation device 17, for example, may have an input and output device, with which a registering of the 3D planning image data set and the 3D radiation image data set may be tripped and monitored. Optionally, the adaptation device 17 may perform this registering in automated fashion. The transformation associated with the registering of the target volume is available to the adaptation device 17 for adapting the irradiation field to a change in position and/or shape of the target volume. The adaptation device 17 uses the transformation to adapt the irradiation field to the changes.

Figure 2:
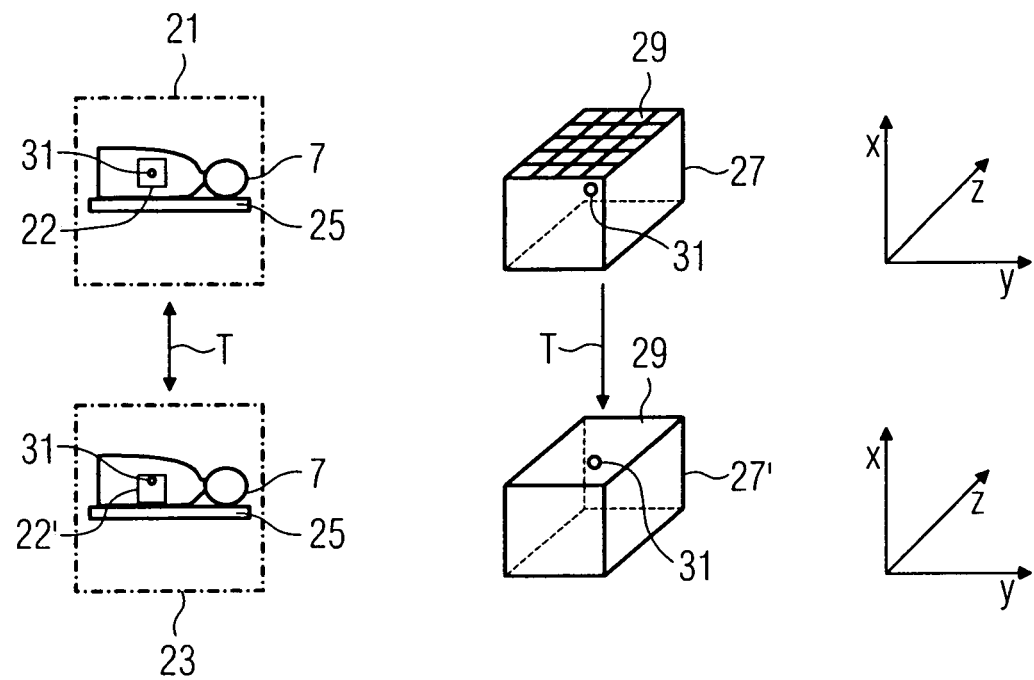
FIG. 2 illustrates one embodiment of an adaptation of an irradiation field.

One embodiment of the adaptation procedure is illustrated in FIG. 2. The 3D planning image data set 21 may be in the form of a rectangle, for example, represented by a schematic upper body of the patient 7 with the target volume 22. A 3D radiation treatment image data set 23 may include a target volume 22 that is displaced in the direction of the patient support 25. This displacement is determined by the adaptation device 17 by the transformation T upon the registering of the two 3D image data sets.

The three-dimensional irradiation field 27 is also shown, with volume elements 29 and with the isocenter 31 located centrally in it. The geometry of the irradiation field 27 upon irradiation is in geometric relationship with the isocenter 31, which may be located in the target volume 22. The adaptation device 17 may cause the transformation T to act on the irradiation field 27, resulting in an adapted irradiation field 27' in which the isocenter 31 is displaced in the X direction and is located in the upper region of the irradiation field.

Figure 3:
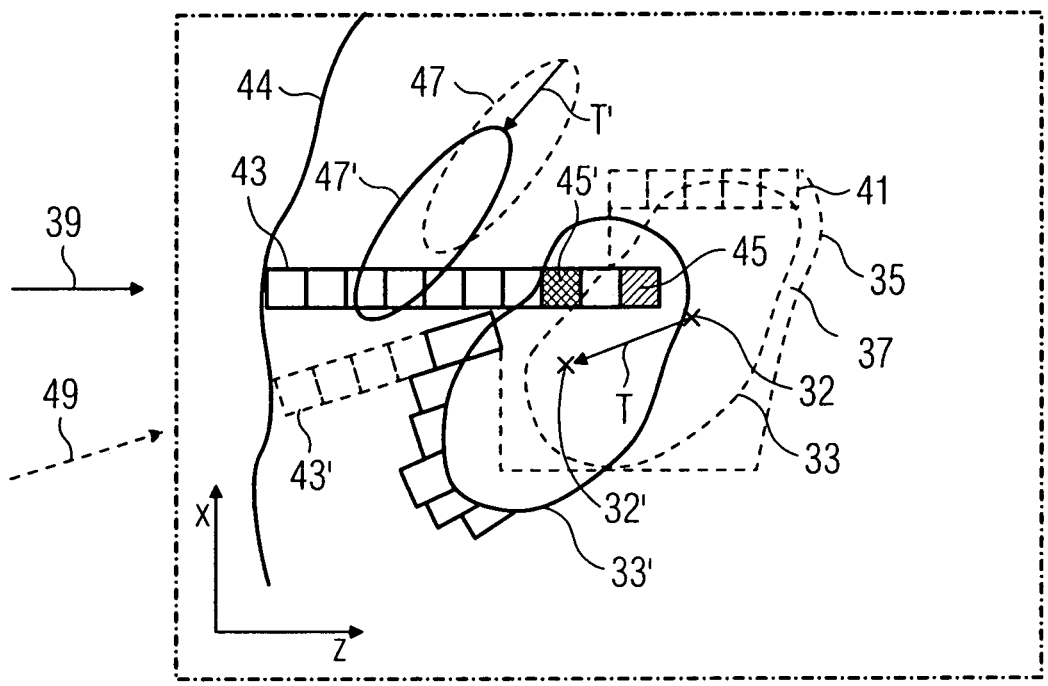
FIG. 3 illustrates the registering of the target volume and a tissue to be spared in the vicinity of the inlet conduit.

FIG. 3 illustrates the possible changes in the event of an exemplary displacement of a target volume 33 (in dashed lines) to a displaced target volume 33' (in solid lines) in accordance with a transformation T. The target volume 33 may have an irradiation field 35, which in its dimensions has only a small safety ring 37. The change in position may be taken into account based on the adaptation made in the irradiation field via the transformation T.

In one embodiment, the irradiation field 35 may cover the position of the displaced target volume 33'. For example, if no adaptation of the irradiation field has been made, then the irradiation field 35 must also cover the position of the displaced target volume 33', which in part is located outside the safety ring 37. In the irradiation, the irradiation field 35 may be irradiated with a particle beam in the Z direction in its entirety, or if the grid scanning technique is used, it may be treated by the irradiation of individual volume elements 41. The dose to be applied to a volume element 41 is calculated in the 3D planning data set with the aid of the attenuation coefficients in the inlet conduit 43. As shown in FIG. 3, an inlet conduit 43 may begin at the body surface 44, for a volume element 45.

In one embodiment, an additional displacement of a tissue region 47 that has increased absorption may be ignored. For example, the additional displacement should be initially ignored. After the displacement T of the target volume 33, the inlet conduit 43 for the volume element 45' of the displaced target volume 33' has been shortened by two volume elements. The same direction of incidence in the particle beam must be reduced in its energy. The required energy may be calculated based on the absorption of the shortened inlet conduit 40. The absorption may be calculated in turn from the 3D radiation treatment image data set.

The displacement T between the isocenters 32 and 32' may be obtained by registering the two image data sets. If the tissue volume 47 that is highly absorbent need not be spared, then the direction of incidence in the Z direction may remain unchanged.

Alternatively, if the tissue volume 47 is to be spared and should not be located in the inlet conduit 43, then by additional registering of the tissue volume 47 and calculation of the associated transformation T', a rotated direction of incidence 49 for the irradiation field may be determined. Based on the rotation, with the doses maintained unchanged in the individual volume elements of the displaced target volume 33', a new grid scale or reshaping of the particle beam is necessary. In FIG. 3, this is shown at the tilted volume elements.

Figure 4:
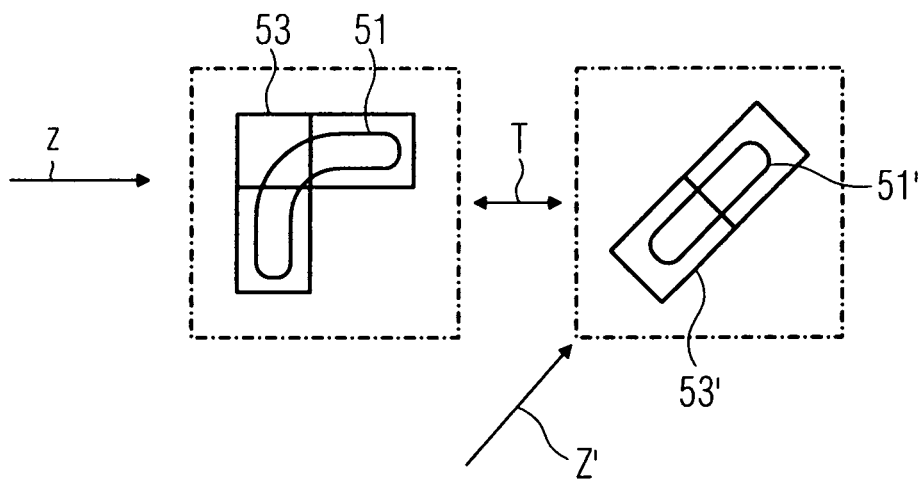
FIG. 4 illustrates changing an irradiation field in the event of translation and deformation of the target volume.

In one embodiment, as shown in FIG. 4, the irradiation field may be adapted to a shape change. In the planning image data set, a curved target volume 51 with an irradiation field 53 comprising three volume elements is planned for irradiation in a direction Z. In the 3D radiation treatment image data set, the target volume expanded and contracted. The altered target volume 51' may be treated with two volume elements of an irradiation field 53'. The dose previously distributed over three volume elements is now distributed over only two volume elements. The transformation T may rotate the direction of incidence Z'.

While the invention has been described above by reference to various embodiments, it should be understood that many changes and modifications can be made without departing from the scope of the invention. For example, although the embodiments were discussed in conjunction with a particle therapy system, the same problems and solutions arise in photon therapy as well. It is therefore intended that the foregoing detailed description be regarded as illustrative rather than limiting, and that it be understood that it is the following claims, including all equivalents, that are intended to define the spirit and scope of this invention.

The invention claimed is:

1. A method for adapting an irradiation field for a radiation treatment procedure on a target volume that is irradiated with a particle beam by scanning a particle beam point by point over the target volume, a position of the target volume, a shape of the target volume, or the position and the shape of the target volume being changeable over time, the method comprising:

obtaining a three-dimensional (3D) planning image data set and the irradiation field, which have been planned by the association of doses to be applied successively with volume elements of the target volume on the basis of the 3D planning image data set, obtaining a 3D radiation treatment data set in a radiation treatment phase, the 3D radiation treatment data set reproducing the target volume to be irradiated, registering the target volume in the 3D planning image data set and the 3D radiation treatment data set to obtain a transformation that describes a change in position, shape, or position and shape of the target volume, and adapting, as a function of the transformation, the irradiation field from the planning to the target volume in the radiation treatment phase, wherein a three-dimensional position of the doses to be successively applied is transformed as a function of the transformation.

2. The method as defined by claim 1, comprising verifying or adapting doses of the irradiation field as a function of a density distribution in the 3D radiation treatment data set in an inlet conduit.

3. The method as defined by claim 1, comprising regularizing the irradiation field as a function of the change in position, shape, or position and shape of the target volume.

4. The method as defined by claim 3, wherein regularizing comprises interpolating the irradiation field to a predetermined radiation treatment grid.

5. The method as defined by claim 1, wherein the registering is manual, partly automated, or automated.

6. The method as defined by claim 1, wherein transformation includes a translation, rotation, scaling, shearing, deformation, or a combination thereof.

7. The method as defined by claim 1, comprising adapting an irradiation direction to a change in position, shape, or position and shape of a surrounding volume that surrounds the target volume.

8. The method as defined by claim 1, comprising generating a warning signal when the change in position, shape, or position and shape of the target volume exceeds a limit value, wherein adapting is performed after disabling the warning signal.

* * * * *